United States Patent [19]

Rawlings

[11] 4,259,276
[45] Mar. 31, 1981

[54] HOLE FORMING

[76] Inventor: Derek S. Rawlings, 71 Cradle Bridge Dr., Willesborough, Ashford, Kent, England

[21] Appl. No.: 917,042

[22] Filed: Jun. 19, 1978

[30] Foreign Application Priority Data

Jun. 24, 1977 [GB] United Kingdom ............... 26671/77

[51] Int. Cl.³ ............................................. B29C 17/10
[52] U.S. Cl. ..................................... 264/68; 264/154;
264/155; 264/156
[58] Field of Search ................... 264/155, 68, 154, 156

[56] References Cited

U.S. PATENT DOCUMENTS

| 2,972,779 | 2/1961 | Cowley | 264/155 |
| 3,562,377 | 2/1971 | Zetzsche | 264/156 |
| 3,688,386 | 9/1972 | Pereira | 264/154 |

FOREIGN PATENT DOCUMENTS 166588 12/1953 Australia ................................. 264/154

Primary Examiner—James H. Derrington
Attorney, Agent, or Firm—Pollock, Vande Sande & Priddy

[57] ABSTRACT

A method of forming holes laterally in the wall of plastics tubing, such as, for example, in medical cannulae, uses a smooth-surfaced, pointed needle. The needle is first forced along its length through the wall of the tubing by a gas-driven motor to form a pierced aperture in the wall. The needle is withdrawn from the aperture and drive is then applied from a gas-driven turbine to rotate the needle at high speed about its longitudinal axis. The needle is then inserted into the pierced aperture, drive to rotate the needle only being applied up to the time of insertion of the needle. Contact of the rotating needle with the rim of the aperture causes the rim contour to be smoothed out. When the needle has ceased to rotate it is withdrawn from the aperture.

8 Claims, 6 Drawing Figures

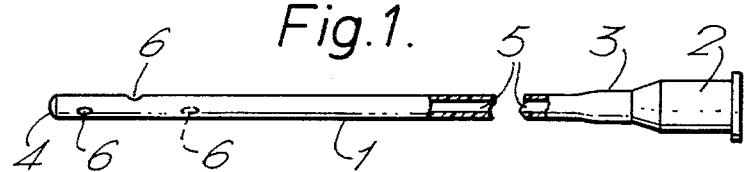
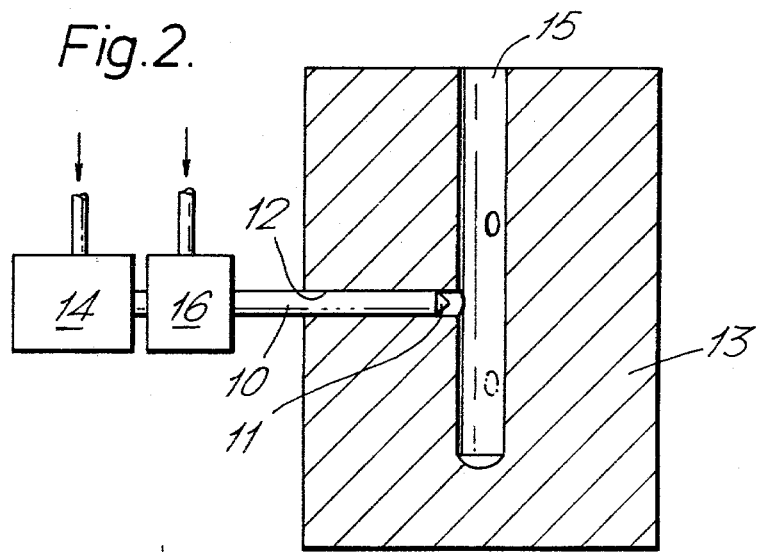
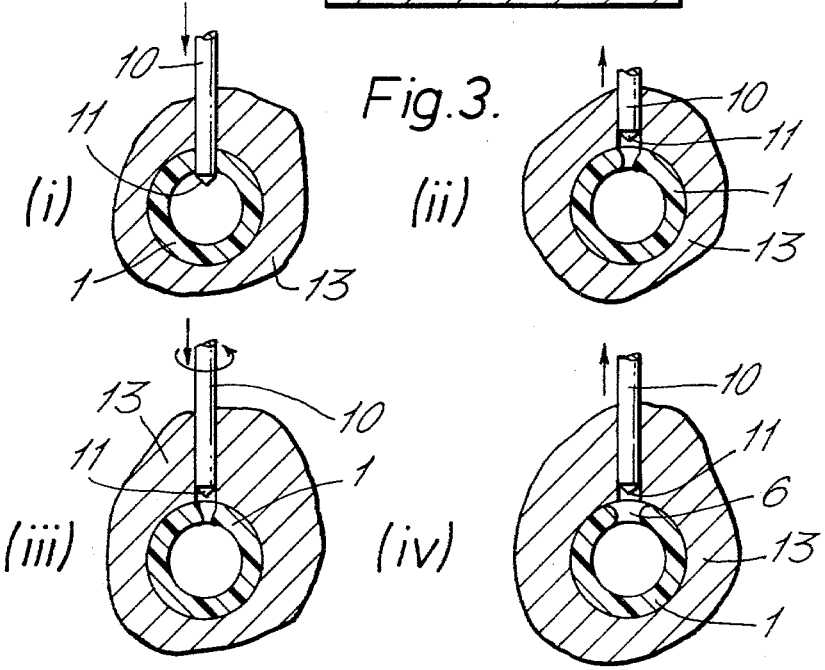

HOLE FORMING

BACKGROUND OF THE INVENTION

This invention relates to methods of hole-forming in plastic workpieces.

The method of the present invention is especially applicable to hole-forming in thin plastic material, but more particularly to the forming of lateral holes in plastic tubing of small diameter. The method is of notable advantage in the manufacture of medico-surgical items, and in particular, of laterally-ported cannulae of small diameter such as used, for example, for epidural anaesthesia.

In the latter respect, an epidural cannula is commonly formed of plastic tubing having a closed distal end and one or more lateral ports or eyes near that end opening from the tube lumen. The eyes are of small diameter and there is difficulty in forming them satisfactorily. More especially, it is present practice to form each eye by punching out a small sector of the tube-wall using a punch that impinges on the tube along a transverse path that is offset from the tube axis to an extent dependent on the cross-sectional area of eye required. There is however considerable difficulty in maintaining uniformity of eye cross-section from one cannula to another with this method, because of the problem of accurate location of the tube relative to the punch. Furthermore, there is also the considerable disadvantage that the punched-out eye is usually rough around its rim.

Epidural cannulae are introduced into the epidural cavity through a hollow metal needle having a sharp pointed tip. The needle is used to puncture the skin and underlying tissue and form a passageway to the epidural cavity, the distal end of the cannula being introduced to the cavity by pushing through the bore of the needle. The needle is subsequently withdrawn by sliding along the cannula. To ensure easy insertion of the cannula through the needle and into the cavity it is important that the rim contour of the lateral eyes in the cannula be as smooth as possible. Furthermore, there is the tendency in unskilled users to push and pull the distal end of the cannula through the introducing needle to overcome the slight frictional resistance of the cannula in the bore of the needle. This can be dangerous since the sharp end of the needle may catch on the cannula and could completely sever the tip from the rest of the cannula. The risk that the end of the needle will catch on the cannula is especially great around the rim of the lateral eyes and it is therefore important that the contour of these rims be as smooth as possible to avoid any such catching. It is important also that the rim of the eyes have a smooth contour to ensure non-irritant placement, as well as free-flow characteristics for fluid passing through the eye.

BRIEF SUMMARY OF THE INVENTION

It is an object of the present invention to provide a method of hole-forming that may be used to alleviate the above-mentioned difficulties.

According to the present invention there is provided a method of hole-forming in a plastic workpiece, wherein a rotating smooth-surfaced tool-element is inserted in a pierced aperture of the workpiece to contact the rim of the aperture and thereby smooth out the rim contour.

With the method of the present invention eye formation in a cannula can be achieved simply and accurately with smooth contour even though the cannula and the eye are both of small diameter.

The pierced aperture may be formed by forcing the tool-element into the workpiece prior to application of drive to rotate the workpiece. Drive to rotate the tool-element may be applied only up to the time of insertion of the tool-element in the pierced aperture.

A cannula and a method of manufacture thereof utilizing the hole-forming method of the present invention, will now be described, by way of example, with reference to the accompanying drawing.

BRIEF DESCRIPTION OF THE DRAWING

FIG. 1 shows the finished cannula;

FIG. 2 illustrates the form of tooling utilized in the manufacture of the cannula of FIG. 1; and FIG. 3 illustrates at (i) to (iv) successive steps in use of the tooling of FIG. 2 in manufacture of the cannula of FIG. 1.

DETAILED DESCRIPTION

Referring to FIG. 1, the finished cannula is formed of nylon tubing 1 having an external diameter of 0.8255 mm and a wall thickness of 0.1778 mm. A conventional Luer connector 2 is coupled into the open, promixal end 3 of the tubing 1, whereas the distal end 4 is occluded, communication from the tubing bore or lumen 5 at the end 4 being provided via three lateral holes or eyes 6. The eyes 6 are spaced from one another longitudinally of the tubing 1 by 3.175 mm and are distributed symmetrically with respect to one another about the tubing circumference. Each eye 6 has a diameter of 0.3556 mm and has a smoothly-contoured rim so as to ensure, in particular, that there is no projection or external roughness to interfere with fluid flow through the eye or insertion of the cannula into, or withdrawal of it from, the epidural cavity or the introducing needle.

The formation of the eyes 6 with smooth contour is achieved by a process that is performed on the tubing 1 before the fitting of the connector 2 and following a heat-sealing step for occluding and rounding-over the end 4. The three eyes 6 are formed simultaneously, and for this the end 4 is inserted into a cylindrical bushing, in which it is a close fit, to be held securely at that end throughout a length of some 19 mm. An air-operated tool is provided at each of the three locations along the bush where the longitudinally and angularly spaced eyes 6 are to be formed in the inserted tubing 1. The three tools are operated together and in their operation and structure are identical to one another. In this latter context the structure and operation of only one of the three tools will be described; tool structure and operation are illustrated in FIGS. 2 and 3 respectively.

Referring to FIG. 2, the tool is in the form of a hardened-steel needle 10 which has a diameter of 0.3556 mm, and which at its pointed tip 11 has an apex angle of 60° degrees. The needle 10 is mounted for movement longitudinally back and forth through an aperture 12 in the wall of the cylindrical bushing 13. An air-powered motor 14 is coupled to the needle 10 to drive it in this way so that the needle tip 11 can be selectively caused to enter from the aperture 12 a limited, but adjustable, distance into the central cylindrical-cavity 15 of the bush 13 and then withdrawn completely into the aperture 12 again. An air-powered turbine 16 is also coupled to the needle 10 for selectively driving it in rotation about its longitudinal axis.

The occluded end 4 of the tubing 1 is inserted into the cavity 15 and the motor 14 operated to drive the needle 10 to pierce through the wall of the tubing 1 within the bush 13, as illustrated at (i) of FIG. 3. The turbine 16 is not operated at this time so that the needle 10 does not rotate during the piercing operation.

The turbine 16 is operated only after the needle 10 has been withdrawn as illustrated at (ii) of FIG. 3 and leaving a raggedly-contoured aperture in the tubing wall. The needle 10 is driven to a rotation speed of some 70,000 revolutions per minute and the motor 14 is again operated to advance the needle 10 as illustrated at (iii) of FIG. 3. Drive of the turbine 16 ceases just as the needle tip 11 is about to re-enter the aperture in the wall of the tubing 1, so that rotation continues during the reinsertion by virtue of the stored rotational energy alone. Contact of the rotating needle 10 with the ragged rim of the aperture produces frictional heating that serves to cause plastic flow smoothing out the eye contour around the needle 10. The energy of the needle 10 is dissipated so that it comes to rest, before being withdrawn as illustrated at (iv) of FIG. 3. A lateral eye is thereby formed having the same diameter as that of the needle 10, and being smoothly contoured to ensure that free flow can be achieved from the tube lumen and that there is no roughness to obstruct insertion or cause irritation during cannulation.

I claim:

1. A method of forming a hole laterally in the wall of plastic tubing comprising the steps of:
   a. piercing said tubing,
   b. inserting a smooth-surfaced needle into the aperture formed by said piercing step,
   c. rotating said needle at high speed about its longitudinal axis while it contacts the rim of said aperture so as to cause frictional heating and consequent plastic flow of the material of said tubing in the region of said aperture and thereby smooth the rim contour, and
   d. withdrawing said needle.

2. A method of hole-forming according to claim 1 wherein said needle has a pointed tip.

3. A method of hole-forming according to claim 2 wherein said pierced aperture is formed by said needle, said needle being forced into said tubing prior to applying said drive to rotate the needle.

4. A method of hole-forming according to claim 3 wherein said needle is forced into said workpiece by means of a gas-driven motor.

5. A method of hole-forming according to claim 1 wherein drive to rotate said needle is applied only up to the time of insertion of the needle in said pierced aperture.

6. A method of hole-forming according to claim 5 wherein said needle is withdrawn from said aperture only after said needle has ceased to rotate.

7. A method of hole-forming according to any one of claims 1 or 2–6 wherein drive to rotate said needle is applied by means of a gas-driven turbine.

8. A method according to any one of claims 1, 2, 3, 4, 5, or 6 wherein said tubing is a cannula.

* * * * *